(12) United States Patent
Messere

(10) Patent No.: US 12,721,380 B2
(45) Date of Patent: Sep. 1, 2026

(54) INHALANT CONTAINMENT DEVICE

(71) Applicant: Joseph Messere, Toronto (CA)

(72) Inventor: Joseph Messere, Toronto (CA)

(73) Assignee: Joseph Messere, Toronto (CA)

( * ) Notice: Subject to any disclaimer, the term of this patent is extended or adjusted under 35 U.S.C. 154(b) by 464 days.

(21) Appl. No.: 18/465,434

(22) Filed: Sep. 12, 2023

(65) Prior Publication Data

US 2025/0082043 A1 Mar. 13, 2025

(51) Int. Cl.

*A24F 47/00* (2020.01)
*A61M 15/00* (2006.01)
*A61M 16/00* (2006.01)

(52) U.S. Cl.

CPC ......... *A24F 47/00* (2013.01); *A61M 15/0021* (2014.02); *A61M 15/0088* (2014.02); *A61M 16/0078* (2013.01)

(58) Field of Classification Search

CPC ..... A24F 42/60; A24F 47/00; A61M 15/0021; A61M 15/0086; A61M 15/0088; A61M 16/0078; A61M 15/0081

See application file for complete search history.

(56) References Cited

U.S. PATENT DOCUMENTS 4,083,374 A 4/1978 Jacobsen
4,807,646 A 2/1989 Sahar
4,922,931 A 5/1990 Nare et al.
D315,617 S 3/1991 Boutte
5,048,545 A 9/1991 Takagi et al.
6,513,524 B1 * 2/2003 Storz .................. A61M 16/208 128/203.29
2008/0029099 A1 * 2/2008 Storz .................. A61M 16/208 128/205.24

(Continued)

FOREIGN PATENT DOCUMENTS

CN 103720052 A 4/2014
CN 214340071 U 10/2021

OTHER PUBLICATIONS

Screen captures from YouTube video clip entitled “How to Attach your Passarolla Vape Balloons for use with the Volcano vaporizer!,” 5 pages, uploaded on Jan. 15, 2022. Retrieved from Internet: <https://www.youtube.com/watch?v=L1kUMNX7igM>.*

(Continued)

*Primary Examiner* — Michael H. Wilson
*Assistant Examiner* — Michael Patrick Mullen
(74) *Attorney, Agent, or Firm* — Daniel Enea; Jordan Sworen; Argus Intellectual Enterprise, LLC

(57) ABSTRACT

An inhalant containment device for capturing smoke or other inhalants is provided. The device includes a mouthpiece that attaches to a bag such that the bag can be filled with smoke, then released at an appropriate time and place. The mouthpiece includes an outer tube that receives an inner tube such that the bag is fed through the outer tube and folded between the inner and outer tube. In this way, the mouthpiece holds the bag securely and keeps a channel open to allow for exhalation of smoke into the bag. A cap is sized to be placed over and close the end of the mouthpiece to keep the smoke in the bag. Additionally, the inhalant containment device may be filled with an inhalant for distribution to patrons at a bar, marijuana dispensary, or other venue.

8 Claims, 3 Drawing Sheets

(56) References Cited

U.S. PATENT DOCUMENTS

| | | | | |
|---|---|---|---|---|
| 2011/0290264 | A1 | 12/2011 | Carse | |
| 2016/0213060 | A1 | 7/2016 | Thaler | |
| 2017/0042223 | A1 | 2/2017 | Park | |
| 2018/0085544 | A1* | 3/2018 | Holyoake ......... | A61M 16/0078 |
| 2019/0125991 | A1* | 5/2019 | Clements .......... | A61M 15/0021 |
| 2020/0008463 | A1 | 1/2020 | Khan-Shaghaghi | |

OTHER PUBLICATIONS

'The Extreme—Q Multi-purpose Hot Air Machine Owners Manual', Arizer, 2021 [retrieved on Jan. 16, 2026]. Retrieved from Internet: https://web.archive.org/web/20211004194823/https://www.swissvaporizer.ch/media/catalog/product/a/r/arizer-extreme-q-user-manual.pdf.*

Smoke Buddy https://smokebuddy.com/ Jun. 13, 2023.

* cited by examiner

INHALANT CONTAINMENT DEVICE

BACKGROUND OF THE INVENTION

The present invention relates to an inhalant containment device. More specifically, the inhalant containment device contains and secures smoke produced during smoking or vaporization activities within a bag that is replaceable.

Recent trends towards smoking, encompassing the consumption of various substances such as tobacco and marijuana, have brought attention to the challenges posed by the emission of smoke in both public and private spaces. As smoking remains a common practice, concerns have arisen regarding the discomfort experienced by nonsmokers due to exposure to smoke. This issue is particularly pronounced in shared living environments, such as apartment buildings, where neighbors often voice their displeasure regarding the pervasive smell of smoke that infiltrates common areas and individual units. Compounding these concerns is the well-established knowledge that secondhand smoke can pose significant health risks, particularly to vulnerable segments of the population, including infants, children, pregnant women, the elderly, and individuals with preexisting health conditions.

Efforts to address these challenges have led to the establishment of designated smoking areas, aiming to segregate smokers from nonsmokers and contain the spread of smoke. Despite these initiatives, conflicts persist, and the effectiveness of separation remains a subject of debate. Moreover, designated smoking areas do not fully address the issue of smoke exposure within residential complexes or the desire for individuals to smoke discreetly without causing disruption.

In view of these developments, there exists a clear need for a device that contains smoke and other inhalants to provide a harmonious balance between the preferences of smokers and nonsmokers. This invention addresses the challenges associated with smoke emission by introducing a novel approach to smoke containment. By allowing smokers to enjoy their chosen activities while minimizing the impact on others in various environments. Move over, the present invention may be utilized within bars, marijuana dispensaries, and the like as a way of providing inhalants to select consumers.

In light of the devices disclosed in the known art, it is submitted that the present invention substantially diverges in design elements and methods from the known art and consequently it is clear that there is a need in the art for an improvement for an inhalant containment device. In this regard the instant invention substantially fulfills these needs.

SUMMARY OF THE INVENTION

In view of the foregoing disadvantages inherent in the known types of inhalant containment devices. The present invention provides a new device for containing smoke and other inhalants while being easily carried and transported to be reused recreationally or disposed of.

It is an objective of the present invention to provide an embodiment of the inhalant containment device having a mouthpiece formed by an inner tube and an outer tube with a bag that secures to the mouthpiece. The bag forms an interior volume configured to store smoke therein. The inner tube and outer tube are configured to concentrically align such that the inner tube is received within the outer tube, wherein the open end of the bag is semi-permanently affixed to the mouthpiece in an in-use configuration such that the mouthpiece forms a channel to provide fluid communication between a distal end of the mouthpiece and the interior volume of the bag.

It is yet another objective of the present invention to provide an embodiment of the inhalant containment device that enables users to discreetly and effectively manage smoke emitted during smoking activities, thereby offering a practical solution for smokers to enjoy their chosen substances without causing discomfort to nonsmokers or compromising their health.

It is yet another objective of the present invention to provide an embodiment of the inhalant containment device that incorporates a bag fitted to a mouthpiece, allowing users to direct exhaled smoke directly into an uninflated bag. The bag is replaceable with any substantially identical bag that is adapted to fit the mouthpiece.

It is an objective of the present invention to provide an embodiment of the inhalant containment device that facilitates the dispersal of the contained smoke in outdoor areas or designated smoking zones, ensuring that the environment is free from lingering smoke and odor. This feature contributes to enhancing the overall experience of users and mitigating the potential impact of smoke on nearby neighbors.

It is another objective of the present invention to provide another embodiment of the inhalant containment device to replicate the model of alcohol sales in bars or pubs. The inhalant containment device allows bars and marijuana dispensary to cater to consumer preferences for discreet and controlled consumption. Vaporized marijuana or tobacco smoke is pre-filled directly into the bag and delivered to the consumer for inhalation.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
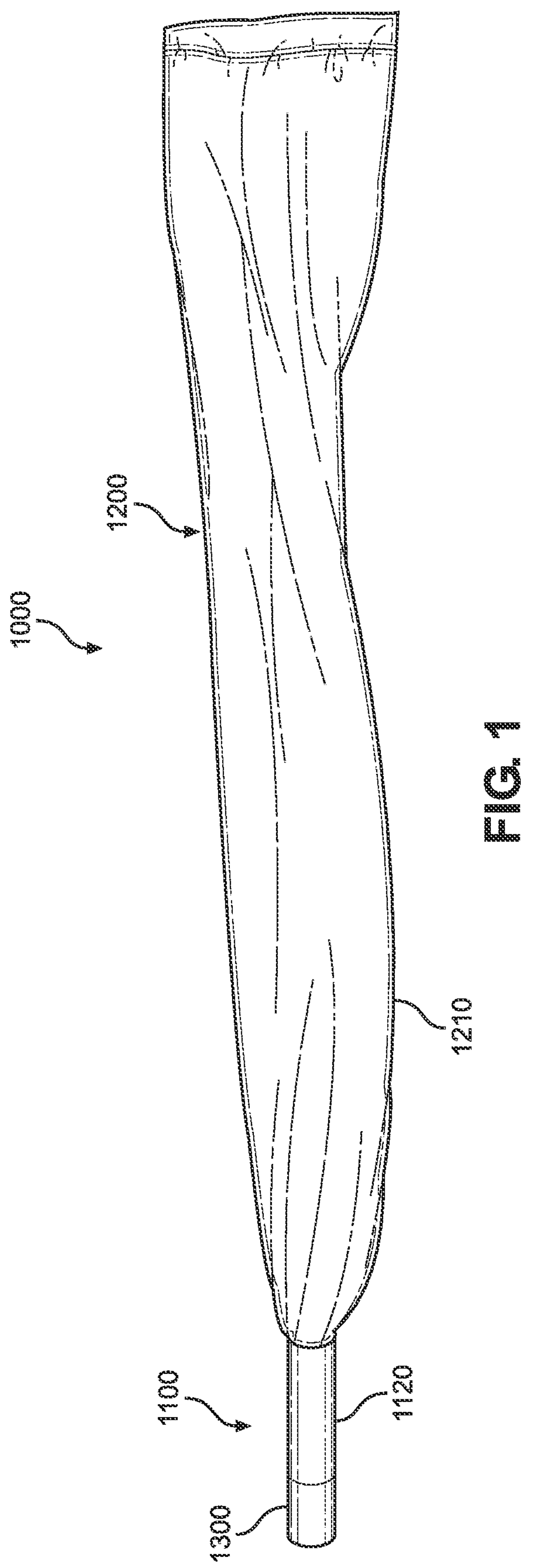
FIG. 1 shows a perspective view of an embodiment of an inhalant containment device.

Reference is made herein to the attached drawings. Like reference numerals are used throughout the drawings to depict like or similar elements of the system. For the purpose of presenting a brief and clear description of the present invention, the embodiment discussed will be used for holding smoke inhalants from an inhalant device. The figures are intended for representative purposes only and should not be considered to be limiting in any respect. Furthermore, the described features, structures, or characteristics may be combined in any suitable manner in one or more embodiments. In the following description, numerous specific details are provided to give a thorough understanding of embodiments.

Reference will now be made in detail to the exemplary embodiment(s) of the invention. References to "one embodiment," "at least one embodiment," "an embodiment," "one example," "an example," "for example," and so on indicate that the embodiment(s) or example(s) may include a feature, structure, characteristic, property, element, or limitation but that not every embodiment or example necessarily includes that feature, structure, characteristic, property, element, or limitation. Further, repeated use of the phrase "in an embodiment," "first embodiment", "second embodiment", or "third embodiment" does not necessarily refer to the same embodiment.

Figure 2:
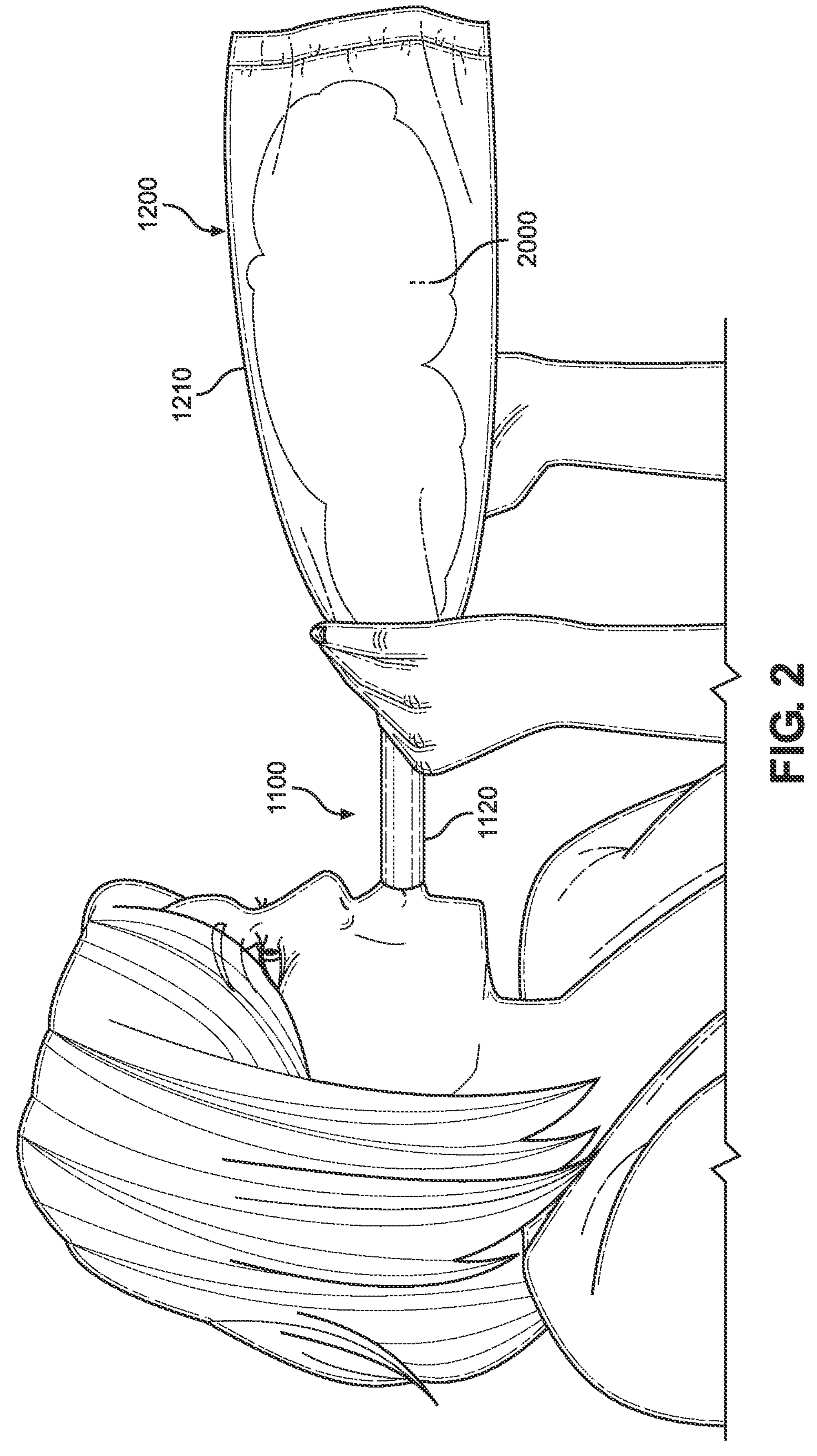
FIG. 2 shows a perspective view of an embodiment of an inhalant containment device in use.

Referring now to FIGS. 1 and 2, there is shown a perspective view of an embodiment of an inhalant containment device and a perspective view of an embodiment of an inhalant containment device in use, respectively. The inhalant containment device 1000 is adapted to contain smoke and other inhalants produced during smoking or vaporization activities. As used hereinafter "inhalant" refers to a gaseous volatile chemical substance that can be inhaled, which may result in mind-altering or other therapeutic effects. Examples of "inhalants" include, but are not limited to tobacco, marijuana, medications (such as nitrites), and the like. "Smoke" is used interchangeably with "inhalant" as a gaseous material. The inhalant containment device 1000 includes a bag 1200 for containing the inhalant, either through exhalation or through prefilling from a vaporizer.

In one embodiment, the inhalant containment device 1000 comprises a mouthpiece 1100 formed by an inner tube 1110 (best shown in FIG. 3) and an outer tube 1120, wherein the inner tube and outer tube 1110, 1120 are configured to concentrically align. As shown in FIGS. 1 and 2, the inner tube 1110 is received within the outer tube 1120 in an assembled configuration. The bag 1200 is secured to the mouthpiece 1100. In the shown embodiment, the bag 1200 includes a sidewall 1210 forming a continuous open end, wherein the open end provides access to an interior volume defined by the sidewall 1210. The interior volume is configured to store the smoke 2000 and the sidewall 1210 comprises an impermeable barrier that contains the smoke 2000 therein.

In the shown embodiment, the inhalant containment device 1000 is in an in-use configuration, wherein the bag 1200 is secured to the mouthpiece 1100. In the in-use configuration, the mouthpiece 1100 provides a channel that extends into the interior volume of the bag 1200 to allow for exhalation of smoke therein. The bag 1200 is held open via the mouthpiece 1100 such that the user places their lips against or therearound the mouthpiece 1100 to form a seal and exhale into the bag 1200. As shown in FIG. 2, the user exhales into a deflated bag 1200 to fill the bag 1200 with smoke. The user may then take the bag inflated with smoke to an outdoor area or an area that is designated for smoking to release the smoke.

In one embodiment, the inhalant containment device 1000 is used as a containment of inhalants for consumers. The bag is filled with an inhalant, such as tobacco or marijuana, via a vaporizer or other device, and distributed to the user. The bag 1200 containing the inhalant includes a metered amount of inhalant which can be inhaled through the mouthpiece 1100.

As shown in FIG. 1, a cap 1300 is configured to close the distal end of the mouthpiece 1100. In one embodiment, the cap 1300 comprises a hollow cylinder having a closed end, wherein the cap 1300 is adapted to fit over the inner tube of the mouthpiece to prevent smoke from within the interior volume of the bag 1200 to pass through the distal end of the mouthpiece 1100.

Figure 3:
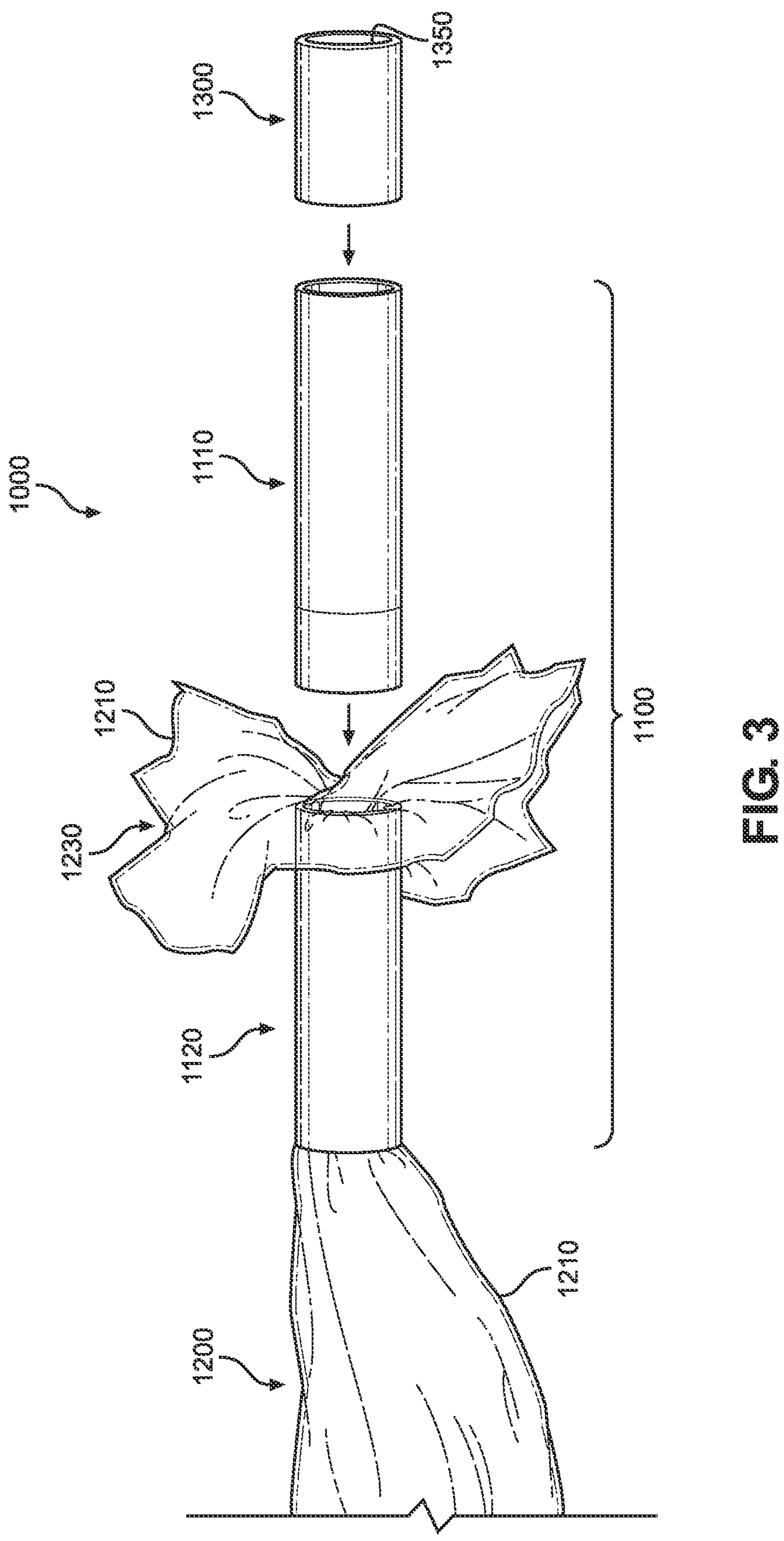
FIG. 3 shows an exploded view of an embodiment of an inhalant containment device.

Referring to FIG. 3, there is shown an exploded view of an embodiment of an inhalant containment device. In the shown embodiment, the bag 1200 includes a continuous open end 1230 that is semi-permanently affixed to the mouthpiece 1100 in an in-use configuration. The inner tube 1110 has a length greater than a length of the outer tube 1120, such that the cap is fitted directly to a section of the inner tube 1110 that extend past the outer tube 1120 when the inner tube 1110 is received by the outer tube 1120. In this way, the inner and outer tubes 1110, 1120 form a shoulder that is adapted to receive the cap 1300, wherein the cap 1300 is sized to fit over the inner tube 1110 and thereby seal the open end of the bag 1200. However, in alternative embodiments, the inner tube 1110 has a length that is equal to the outer tube 1120, such that the cap 1300 is fitted directly to the outer tube 1120. The inner tube 1110 and the outer tube 1120 are removable from each other.

In the shown embodiment, in an in-use confirmation, the sidewall 1210 of the bag 1200 is positioned within the outer tube 1120 and folded over a distal end of the outer tube 1120. The inner tube 1110 is then fed through the distal end of the outer tube 1120, thereby sandwiching the bag 1200 between the inner and outer tubes 1110, 1120. In this way, the mouthpiece 1100 forms a channel to provide fluid communication between a distal end of the mouthpiece 1100 and the interior volume of the bag 1200. The outer tube 1120 is concentrically aligned with the inner tube 1110 and is slightly larger so as to fit the bag 1200 therebetween while frictionally engaging the inner tube 1110. When the outer tube 1120 slides over the bag 1200 and receives the inner tube 1110, the bag is held open to allow the user to blow smoke into the interior volume or to inhale the contents of the bag. A cap 1300 is adapted to engage over the distal end of the mouthpiece 1100 to seal the channel of the mouthpiece. In the shown embodiment, the cap 1300 comprises a cylinder having a closed end. In alternative embodiments, other caps or lids may be used to control the flow of fluid through the mouthpiece.

In an alternative embodiment, the inner tube 1110 receives the open end of the bag, wherein the bag is pulled back over an exterior of the inner tube 1110. The outer tube 1120 is then positioned to receive the inner tube 1110 and bag 1200 to position the bag between the tubes 1110, 1120 and thereby provide access to the interior of the bag 1200 through the open end of the mouthpiece 1100. In this embodiment, the tolerance between the inner and outer tube 1110, 1120 may be larger than the first embodiment to fully receive the inner tube 1110 by the outer tube 1120. Additionally, in one embodiment, the inner tube 1110 includes a stop that seats the outer tube 1120 in a desired position. The cap 1300 is configured to secure to the open end of the mouthpiece 1100.

In one embodiment, the cap includes an indicator 1350 that distinguishes one device from a substantially similar device. For example, a first indicator may be used to distinguish a first device filled with a first smoke from a second device filled with a second smoke. Alternatively, multiple users may use the indicator to identify their device from other user's devices. In one embodiment, the indicator includes a color or alphanumerical indicator. In the shown embodiment, the indicator 1350 is positioned at an exterior side of the closed end of the cap 1300. In alternative embodiments, the indicator 1350 may be located on the mouthpiece or the bag.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An inhalant containment device, comprising:

a mouthpiece formed by an inner tube and an outer tube, wherein the inner tube and the outer tube are removable from each other;

and a bag having a sidewall forming a continuous open end, the bag having an interior volume configured to store smoke therein;

wherein the inner tube and outer tube are configured to concentrically align such that the inner tube is received within the outer tube;

wherein the continuous open end of the bag is removably affixed to the mouthpiece in an in-use configuration, wherein in the in-use configuration, the sidewall of the bag is positioned within the outer tube and folded over a distal end of the outer tube so as to be positioned between the inner tube and outer tube, and such that the mouthpiece forms a channel to provide fluid communication between a distal end of the mouthpiece and the interior volume of the bag.

2. The inhalant containment device of claim 1, wherein in the in-use configuration, the bag frictionally couples the inner tube and outer tube and forms a seal therebetween.

3. The inhalant containment device of claim 1, further comprising a cap configured to close the distal end of the mouthpiece.

4. The inhalant containment device of claim 3, wherein the cap comprises a hollow cylinder having a closed end, wherein the cap is adapted to fit over the inner tube to prevent smoke from within the interior volume of the bag to pass through the distal end of the mouthpiece.

5. The inhalant containment device of claim 1, wherein the bag is prefilled with an inhalant agent.

6. The inhalant containment device of claim 5, wherein the inhalant agent is tobacco or marijuana.

7. The inhalant containment device of claim 5, wherein the bag is prefilled with a metered amount of the inhalant agent.

8. A method of securing an inhalant within a bag, comprising:

providing an inhalant containment device, having:

a mouthpiece formed by an inner tube and an outer tube, wherein the inner tube and the outer tube are removable from each other;

and a bag having a sidewall forming a continuous open end, the bag having an interior volume configured to store smoke therein;

wherein the inner tube and outer tube are configured to concentrically align such that the inner tube is received within the outer tube;

wherein the continuous open end of the bag is removably affixed to the mouthpiece in an in-use configuration, wherein in the in-use configuration, the sidewall of the bag is positioned within the outer tube and folded over a distal end of the outer tube so as to be positioned between the inner tube and outer tube, and such that the mouthpiece forms a channel to provide fluid communication between a distal end of the mouthpiece and the interior volume of the bag;

filling the bag with the inhalant via the channel formed by the mouthpiece; and securing the inhalant within the bag by placing a cap over an opening of the mouthpiece.

* * * * *